(12) United States Patent
Fladl et al.

(10) Patent No.: US 8,763,562 B2
(45) Date of Patent: Jul. 1, 2014

(54) WEARABLE MEDICAL TUBING AND CABLING CONTAINMENT HARNESS

(75) Inventors: Theresia Trevan Fladl, Ingolstadt (DE); Thomas Lloyd Bellaire, Burnaby (CA); Ernie Janzen, Burnaby (CA)

(73) Assignee: British Columbia Institute of Technology, Burnaby, British Columbia (CA)

( * ) Notice: Subject to any disclaimer, the term of this patent is extended or adjusted under 35 U.S.C. 154(b) by 738 days.

(21) Appl. No.: 12/682,373

(22) PCT Filed: Oct. 8, 2008

(86) PCT No.: PCT/CA2008/001783
§ 371 (c)(1),
(2), (4) Date: Sep. 7, 2010

(87) PCT Pub. No.: WO2009/046523
PCT Pub. Date: Apr. 16, 2009

(65) Prior Publication Data
US 2010/0325772 A1       Dec. 30, 2010

Related U.S. Application Data

(60) Provisional application No. 60/978,627, filed on Oct. 9, 2007.

(51) Int. Cl.
*A41D 13/00* (2006.01)
(52) U.S. Cl.
USPC .............................................. 119/850; 2/102
(58) Field of Classification Search
CPC ...................... A01D 13/1245; A01D 13/1272; A01D 13/1281
USPC ....................................... 119/850; 2/102, 106
See application file for complete search history.

(56) References Cited

U.S. PATENT DOCUMENTS 4,512,437 A * 4/1985 Savage .............................. 182/3
4,623,316 A * 11/1986 Ratliff ........................... 441/106
(Continued)

FOREIGN PATENT DOCUMENTS

CA     1 180 623 A1    1/1985
CA     2 148 375 A1    5/1994
(Continued)

OTHER PUBLICATIONS

International Search Report in PCT/CA2008/001783 having a mailing date of Nov. 21, 2008.
(Continued)

*Primary Examiner* — Rob Swiatek
*Assistant Examiner* — Justin Benedik
(74) *Attorney, Agent, or Firm* — Ryan W. Dupuis; Kyle R. Satlerthwaite; Ade & Company Inc.

(57) ABSTRACT

A wearable tubing safety vest configured to harness medical treatment delivery tubing and/or communication cables. The tubing safety vest comprises a vest component having a body-encompassing component cooperable with a plurality of releasably securable flaps, and an elongate tubing harness configured to releasably receive and retain therethrough at least one of medical treatment delivery tubing and communication cables. The tubing harness may be securely engaged with the vest component or alternatively, at least one hinge component can be interposed the vest component and the tubing harness. The vest component is configured for demountably encircling a mammalian body torso, e.g, a human infant torso, juvenile torso, or an adult torso. The tubing harness may be demountably engaged with the front or with the back of the vest component. The wearble tubing safety vest may be optionally configured for demountable engagement about an animal's torso.

14 Claims, 13 Drawing Sheets

(56) References Cited

U.S. PATENT DOCUMENTS

| | | | |
|---|---|---|---|
| 4,688,270 A * | 8/1987 | Denicola et al. | 2/102 |
| 5,211,321 A * | 5/1993 | Rodriguez | 224/604 |
| 5,334,186 A * | 8/1994 | Alexander | 604/180 |
| 5,611,085 A * | 3/1997 | Rasmussen | 2/102 |
| 5,628,725 A | 5/1997 | Ostergard | |
| 5,676,294 A * | 10/1997 | Eklund et al. | 224/625 |
| 6,065,154 A * | 5/2000 | Hulings et al. | 2/102 |
| 6,450,168 B1 * | 9/2002 | Nguyen | 128/869 |
| 6,487,725 B1 * | 12/2002 | Jordan | 2/94 |
| 6,571,395 B1 | 6/2003 | Korkor | |
| 6,681,404 B1 * | 1/2004 | Adlard et al. | 2/94 |
| 7,418,741 B2 * | 9/2008 | Rogers | 2/114 |
| 2002/0165495 A1 * | 11/2002 | Bird et al. | 604/179 |
| 2004/0226073 A1 | 11/2004 | McCullar | |
| 2006/0206978 A1 * | 9/2006 | Hilton et al. | 2/104 |

FOREIGN PATENT DOCUMENTS

| | | |
|---|---|---|
| DE | 202006017975 | 3/2007 |
| EP | 0 075 753 A1 | 4/1983 |
| WO | 9409655 | 5/1994 |

OTHER PUBLICATIONS

Written Opinion of the International Searching Authority in PCT/CA2008/001783 having a mailing date of Nov. 21, 2008.

International Preliminary Report on Patentability in PCT/CA2008/001783 having a date of completion of Jan. 7, 2010.

Drago, Dorothy A., et al., "Infant Mechanical Suffocation Deaths in the United States, 1980-1997," Pediatrics, May 1999, vol. 103, No. 5, pp. e59-e71.

Nakamura, Suad Wanna et al., "Suction-Type Suffocation Incidents in Infants and Toddlers," Pediatrics, Jan. 2003, vol. 111, No. 1, pp. e12-e16.

Scheers, N. J. et al., "Where Should Infants Sleep? A Comparison of Risk for Suffocation of Infants Sleeping in Cribs, Adult Beds, and Other Sleeping Locations," Pediatrics, Oct. 2003, vol. 112, No. 4, pp. 883-889.

Garros, Daniel et al., "Strangulation With Intravenous Tubing: A Previously Undescribed Adverse Advent in Children," Pediatrics, Jun. 2003, vol. 111, No. 6, pp. e732-e734.

* cited by examiner

WEARABLE MEDICAL TUBING AND CABLING CONTAINMENT HARNESS

This is a national stage application of PCT/CA2008/001783, filed internationally on Oct. 8, 2008, which claims priority to U.S. Provisional Application No. 60/978,627, filed on Oct. 9, 2007.

TECHNICAL FIELD

This invention relates to infant safety devices. More particularly, this invention relates to safety devices configured for prevention of infant entanglement with installed medical treatment delivery tubes, medical instrument and equipment cables, and the like.

BACKGROUND OF THE INVENTION

The potential for infant or child strangulation and/or asphyxia in the home environment is well documented in the health care literature (Drago et al., 1999, Pediatrics 103: 59-71; Nakamura et al., 2003, Pediatrics 111: 12-16; Scheers et al., 2003, Pediatrics 112 : 883-889). Strangulation by entanglement is the sixth leading cause of infant mechanical suffocation in the United States (Drago et al.), while in Canada, 19 per 100,000 deaths were attributed to suffocation in the 0 to 4 years age group (Beaulne, 1997, *'For the Safety of Canadian Children and Youth: From Inury Data to Preventative Measures'*, Health Canada Publ.).

Children in hospitals are also at risk for strangulation or asphyxia caused by entanglement. The risk is directly associated with tubings and lines associated with the delivery of intravenous fluids, oxygen therapy, cardiorespiratory monitoring, and other treatments and diagnostic techniques (Garros et al., 2003, Pediatrics 111: 732-734). The percentage of hospitalized pediatric patients who receive intravenous (IV) therapy is significant. The length of IV tubing varies between 2.1 and 2.7 meters to accommodate the distance from the patient in the bed/crib to the IV pump (used to maintain even rates of fluid administration) which is similar to the lengths of blind or window cords, and therefore, IV tubing is also a significant risk factor for infant entanglement and strangulation. Depending on fluid requirements and drug therapy, an infant or child may have several tubing lines leading to multiple pumps, as well as oxygen or other monitoring or therapeutic tubes or lines. Reports of children dying in hospital by strangulation via tubing and monitor wires are found in the literature (Garros et al.). Further, nurses describe finding children entangled in tubing, however are unlikely to report the occurrence unless harm is identified. Although the incidence of tubing entanglement is largely unknown, the potential consequences of serious injury and death are unacceptable. The population at risk is identified as infants between 3 and 36 months as well as cognitively incapacitated children, adolescents and adults.

SUMMARY OF THE INVENTION

The exemplary embodiments of the present invention are directed to tubing safety vests configured for comfortable and secure installation about a subject's torso, while harnessing and containing therethrough medical treatment delivery tubing, instrument and equipment cables, and the like.

According to an exemplary embodiment of the present invention, the tubing safety vest comprises a vest component and a tubing harness component. The vest component is configured to wrap around the subject and is secured in place with at least three flaps configured to demountably engage suitable portions of the safety vest. The tubing harness component is securely engaged with the vest component, and extends from about the upper end to the bottom end of the vest component such that, after installation of the tubing safety vest onto a subject, the upper end of the tubing harness component is positioned front-facing about the subject's shoulder while the lower end of the tubing harness is positioned front-facing about the subject's upper leg. The tubing harness may be optionally positioned back-ward facing behind the subject if so desired.

According to one aspect, a first flap is provided at about the bottom end of the safety vest and is configured to encircle an upper thigh of the subject and engage an opposing portion of the safety vest. A second flap is provided about one upper end of the safety vest and is configured to encircle the subject's upper chest area and demountably engage an opposing portion of the safety vest. A third flap is provided at one upper end of the safety vest and is configured to encircle the subject's shoulder—armpit area on the same side as the encircled thigh and demountably engage an opposing portion of the safety vest. This configuration is designed to prevent movement of the vest along the long axis of the body, and to prevent twisting of the vest around the torso.

According to another aspect, a first set of opposing flaps is provided at about the bottom end of the safety vest and are configured to encircle an upper thigh of the subject. A second set of opposing flaps is provided about the upper end of the safety vest and are configured to encircle the subject's upper chest area. A third set of flaps is provided at the upper end of the safety vest and are configured to encircle the subject's shoulder—armpit area on the same side as the encircled thigh.

According to another aspect, each of the flaps is provided with at least one releaseably cooperating fastening device exemplified by buttons, hooks and eyes, clasps, snaps, Velcro® strips (Velcro is a trademark of Velcro Industries B.V. Ltd. Liab. Co., Curacao, Netherlands, Antilles), and the like.

According to yet another aspect, the tubing harness component comprises an elongate panel configured to extend from about the first set of flaps to about the third set of flaps of the vest component. The elongate panel is securely attached to the vest component by stitching or other such methods, such that two opposing elongate half-panels are formed, said elongate half-panels foldable together. The other edges of the opposing elongate half-panels are provided with releasably cooperating fastening devices extending from the upper end to the lower end of the tubing harness thereby enabling a caregiver to easily install and to remove lengths of tubing and/or cable therein. Suitable releaseably cooperating fastening devices are exemplified by buttons, hooks and eyes, clasps, snaps, Velcro® strips, and the like.

According to a further aspect, the vest component and the tubing harness component comprise suitable fabric-like materials. The fabric-like materials may comprise natural and/or synthetic materials. The materials may be selected for one-time use only, after which they are appropriately disposed of. Alternatively, the materials may be selected for their washable properties.

BRIEF DESCRIPTION OF THE DRAWINGS

The present invention will be described in conjunction with reference to the following drawing, in which.

DETAILED DESCRIPTION OF THE INVENTION

Figure 1:
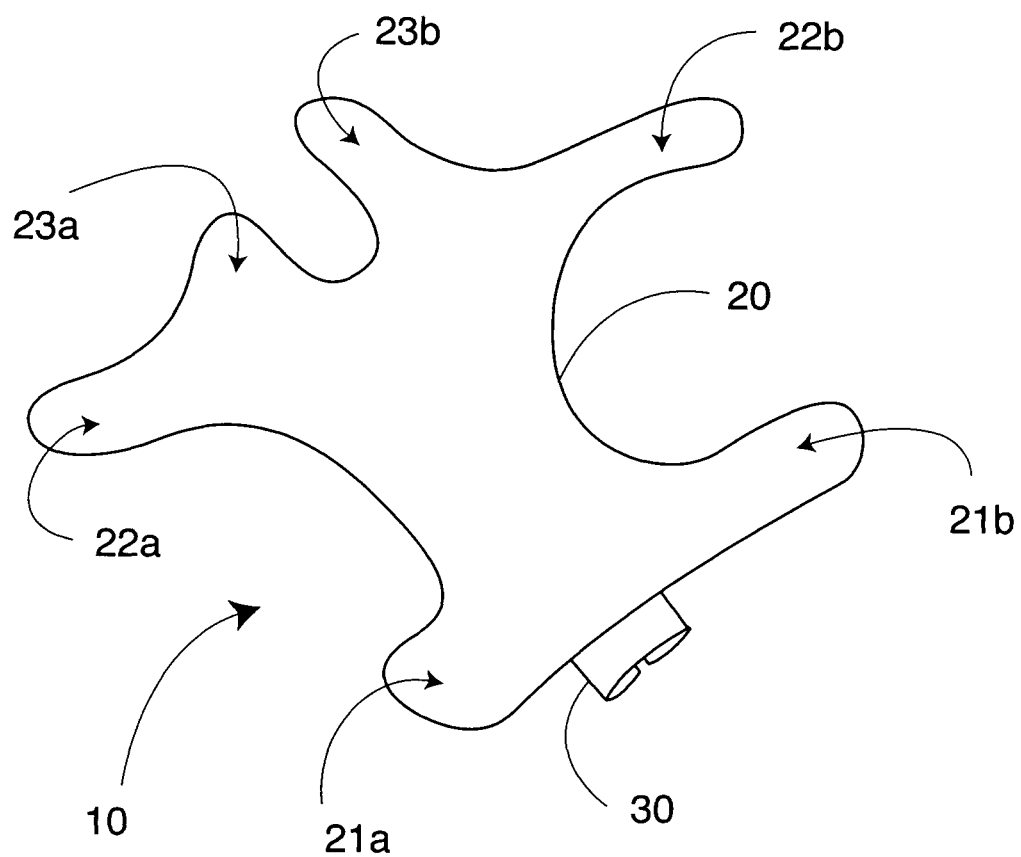
FIG. 1 is a plan view of an exemplary embodiment of a medical treatment delivery tubing safety vest of the present invention.
Figure 2:
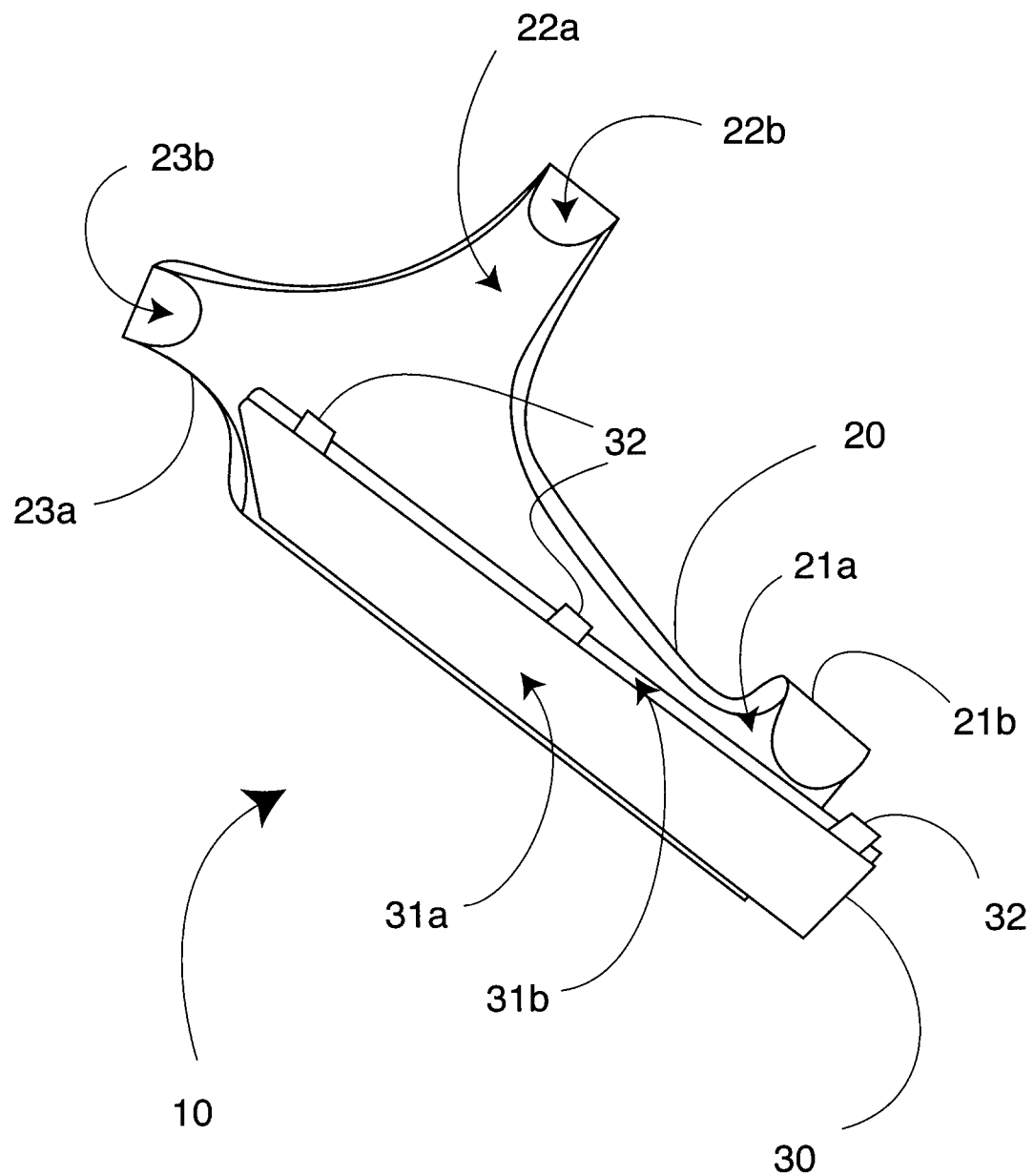
FIG. 2 is a front view of the embodiment from FIG. 1, folded together showing the tubing harness aspect of the present invention.
Figure 3:
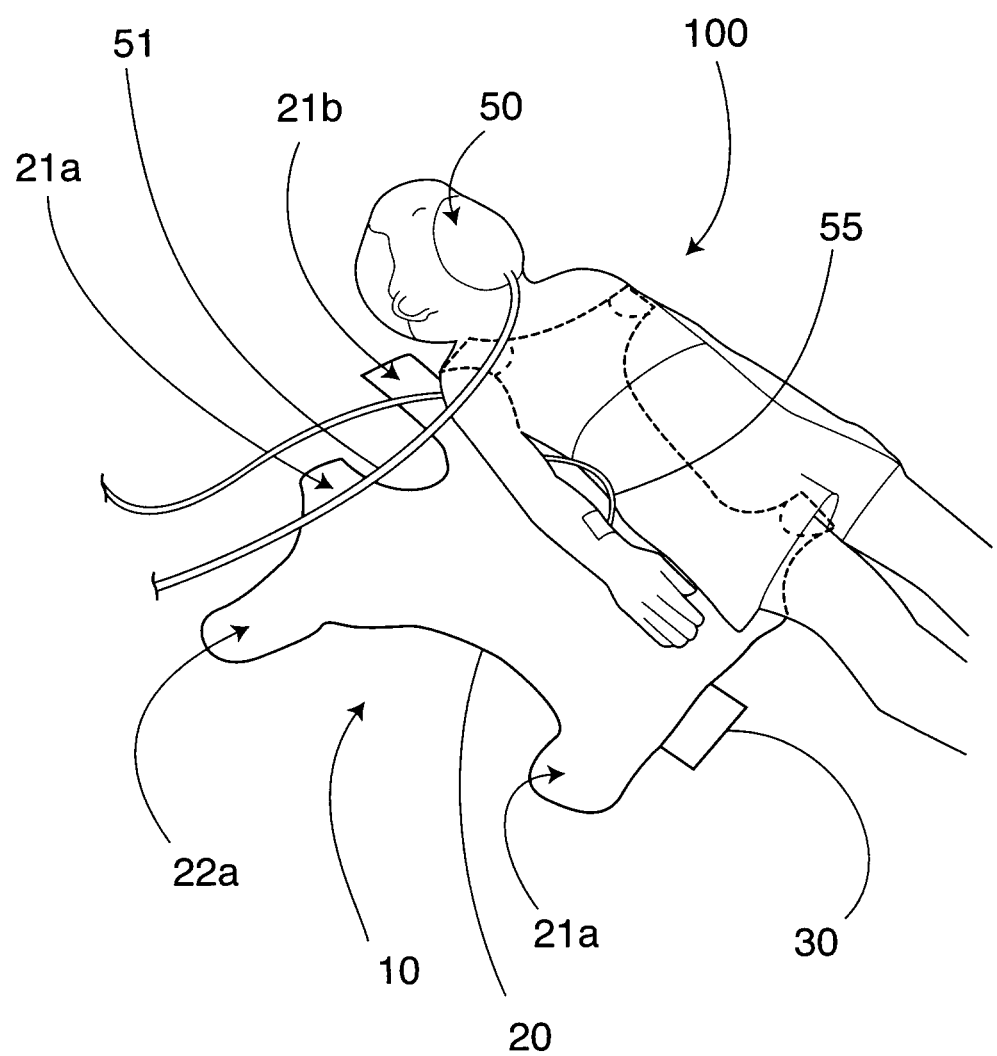
FIG. 3 is a perspective view showing an infant being placed onto the embodiment shown in FIG. 1.

Exemplary embodiments of the present invention are directed to medical tubing safety vests for harnessing and containing therein and therethrough delivery tubing for medical treatments. The tubing safety vests are configurable for: (a) installation about human infant and juvenile body torsos, and (b) for securely encasing medical treatment delivery tubing and or physiological monitoring cables, such that the potential for entanglement of the tubing and cabling about the wearers' neck, throat and head areas is significantly reduced. The tubing safety vests can be configured in a variety of sizes suitable to comfortably and securely encompassing the torsos and one lower appendage of infants and juveniles ranging in age from birth through late adolescence. It is within the scope of the invention to configure medical tubing safety vests as disclosed herein for installation about larger human torsos, i.e., adults. It is also within the scope of the present invention to configure the tubing safety vests disclosed herein for fitting about animal torsos e.g., cats, dogs, livestock, equines and exotic animals and the like, for harnessing therethrough tubing provided for delivery of veterinary treatments and/or cables connected to instruments and/or equipment configured for monitoring vital signs and the like.

An exemplary embodiment infant/juvenile medical tubing safety vest 10 of the present invention is shown in FIGS. 1-6 and generally comprises a vest component 20 and a tubing harness component 30. The vest component 20 comprises a washable fabric-type material provided with, for example, three pairs of releasably cooperating flaps configured for encircling a portion of a wearer's torso. The first set of flaps 21a, 21b is configured to encircle the upper thigh area of one of the wearer's legs. The second set of flaps 22a, 22b is configured to encircle the wearer's upper chest area. The third set of flaps 23a, 23b is configured to encircle one of the wearer's upper shoulder—armpit areas. The pairs of releasably cooperating flaps are provided with suitable releaseably cooperating fastening devices exemplified by: (a) buttons and buttonholes, (b) Velcro® strips, (c) snaps, (d) hook and eye clasps, (e) adhesive strips, and the like. It is to be noted that it is suitable to provide a plurality of cooperating devices on each of the flaps thereby providing a plurality of fastening options to adjustably accommodate anatomical variations amongst subjects, and also, making it possible to tighten or loosen the vest component about the subject for safety and/or comfort.

An elongate tubing harness 30 is securely engaged with the vest component 20 with the top of the tubing harness 30 generally positioned in between the third set of flaps 23a, 23b, while the bottom of the tubing harness 30 is generally positioned in between the first set of flaps 21a, 21b and extends therebeyond. The tubing harness 30 is configured to releasably secure therein one, or alternatively, a plurality of medical treatment delivery tubing exemplified by IV tubing, respirator/ventilator tubing, and with cabling communicating with physiological monitoring devices and treatment administration devices e.g., ECG cables and the like. As exemplified in FIGS. 1 and 2, the tubing harness 30 may comprise an elongate flexible washable fabric-type material that may be folded together and releasibly secured by fastening devices 32 provided along the opposing elongate edges. Suitable releasible fastening devices are exemplified by Velcro® flaps 32 (FIG. 2), hook and eye clasps, button/buttonholes, snaps, and the like. It is preferable that the inner surface area 33 of the tubing harness 30 comprises a pliable non-slip material that is engaged with the material comprising the tubing harness 30, for the purpose of engaging and retaining thereagainst tubing and/or cabling placed therein. Suitable non-slip materials are exemplified by plastics, resinous e.g., resin-impregnated fibrous materials, and the like.

Figure 4:
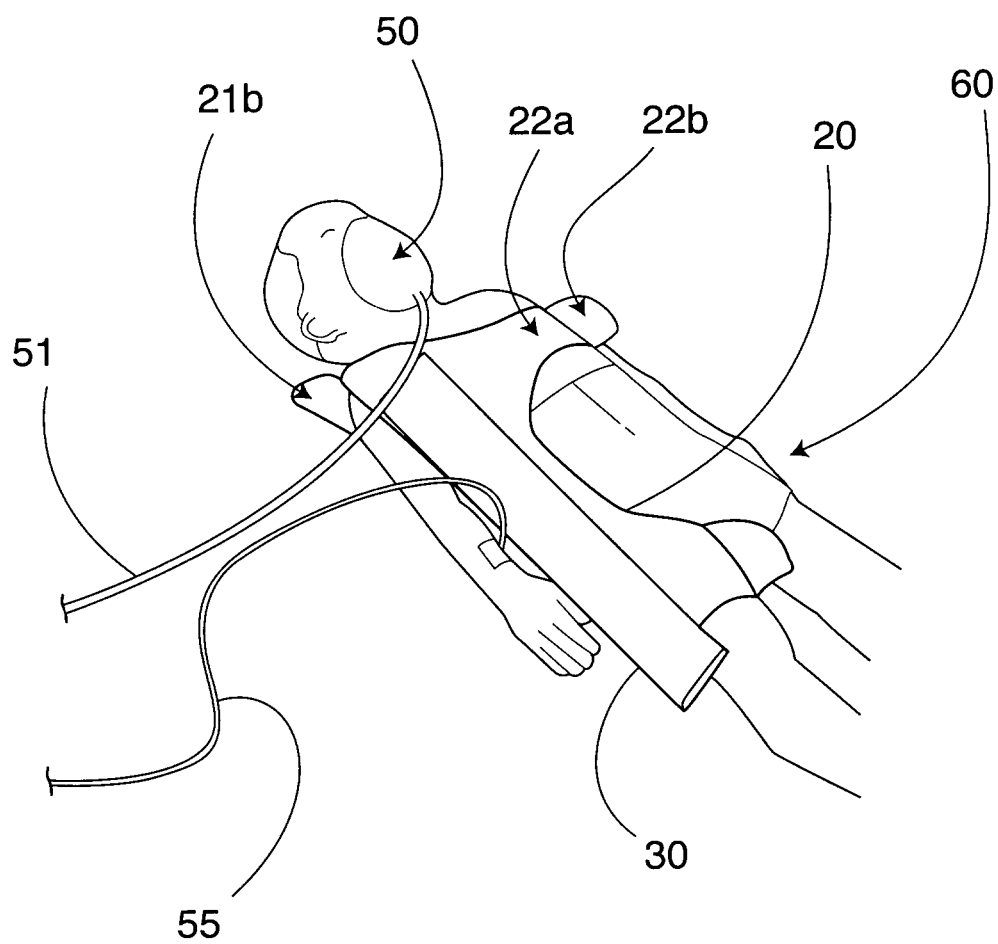
FIG. 4 is a perspective view showing the tubing safety vest from FIG. 3 being fastened about the infant.
Figure 5:
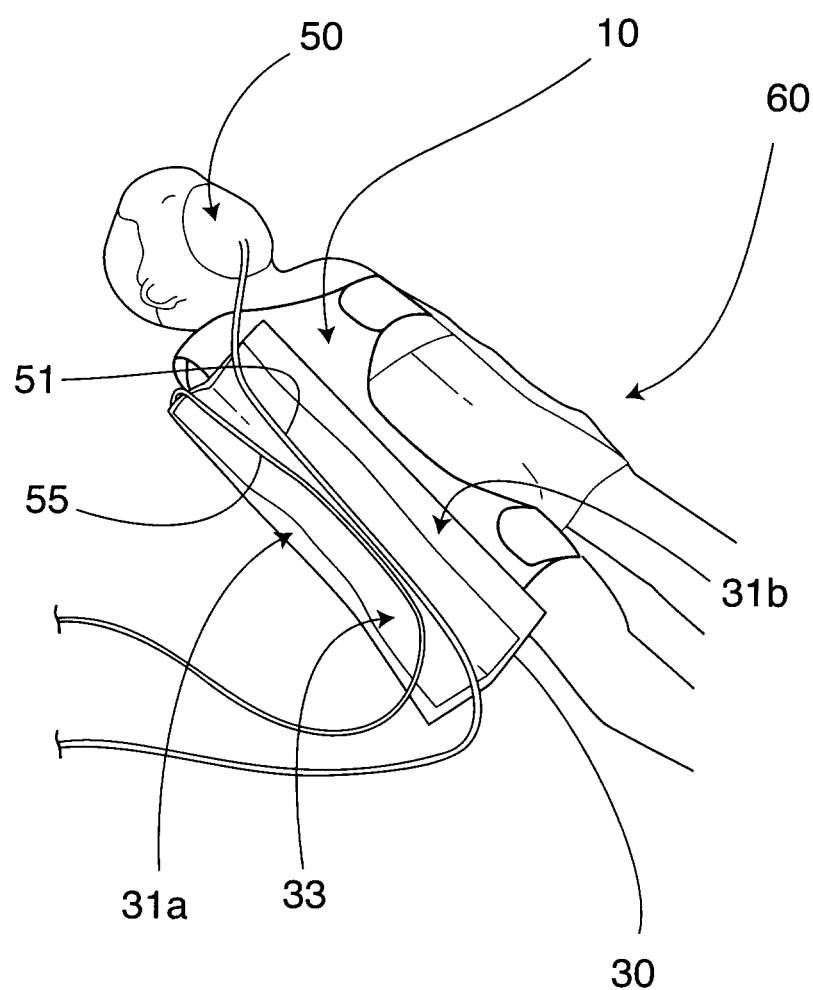
FIG. 5 is a perspective view showing the ventilator and IV tubes being secured into the tubing harness.
Figure 6:
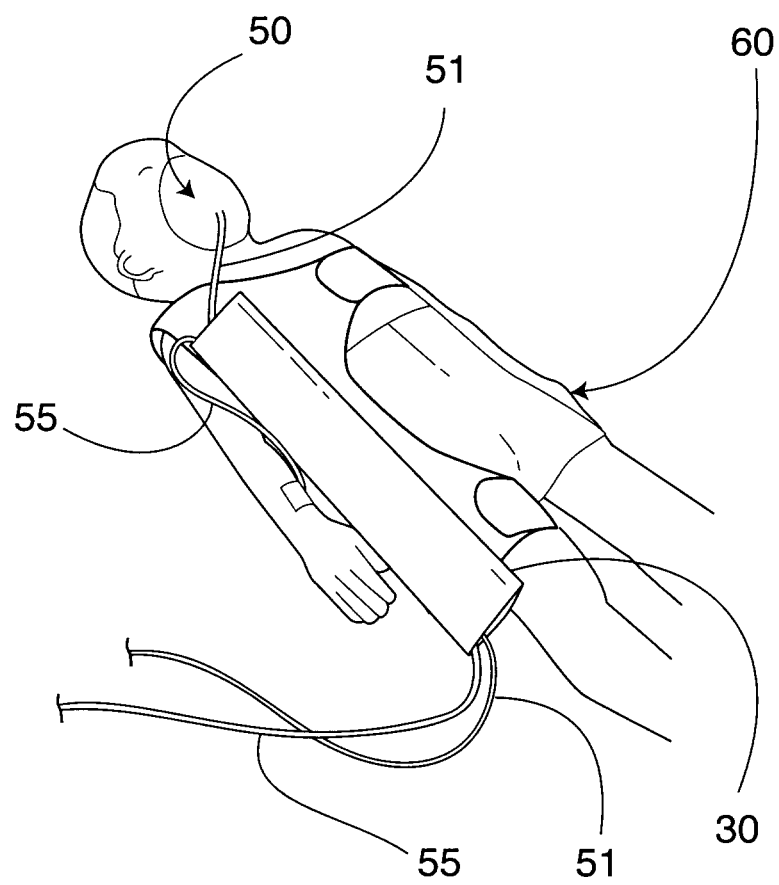
FIG. 6 is a perspective view showing the tubing safety vest from FIG. 3 fully installed about the infant.
Figure 7:
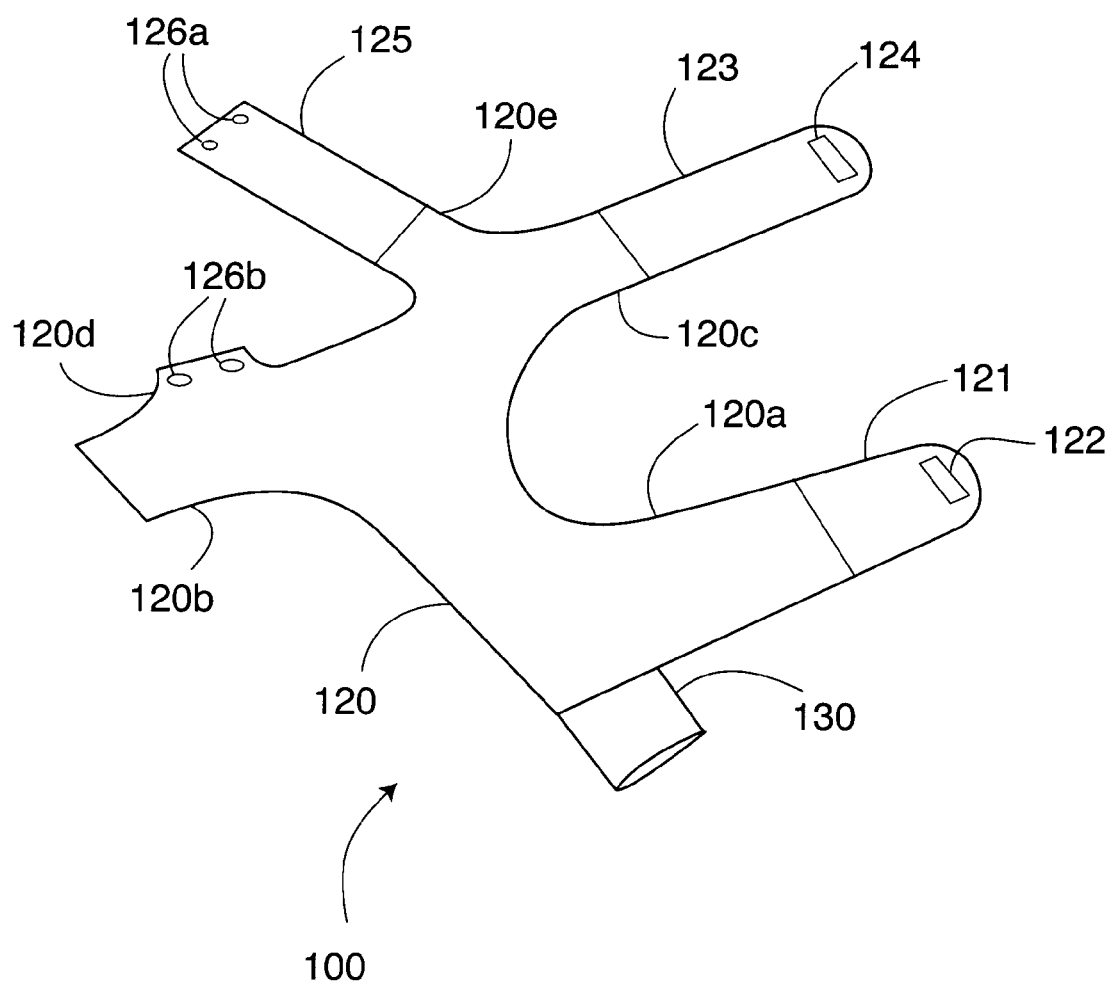
FIG. 7 is a plan view of another exemplary embodiment of a medical treatment delivery tubing safety vest of the present invention.
Figure 8:
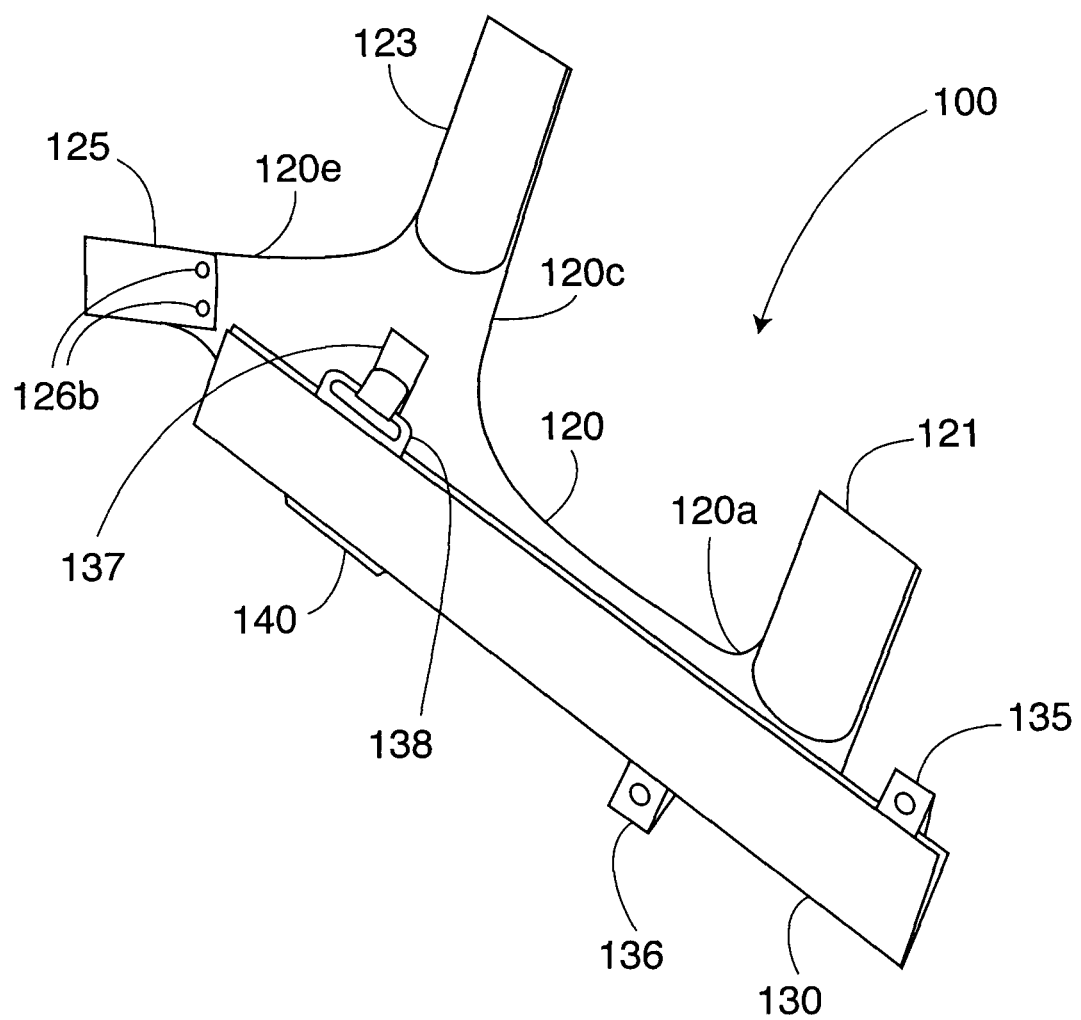
FIG. 8 is a front view of the embodiment from FIG. 8, showing the tubing harness aspect of the present invention fastened to the safety vest component.
Figure 9:
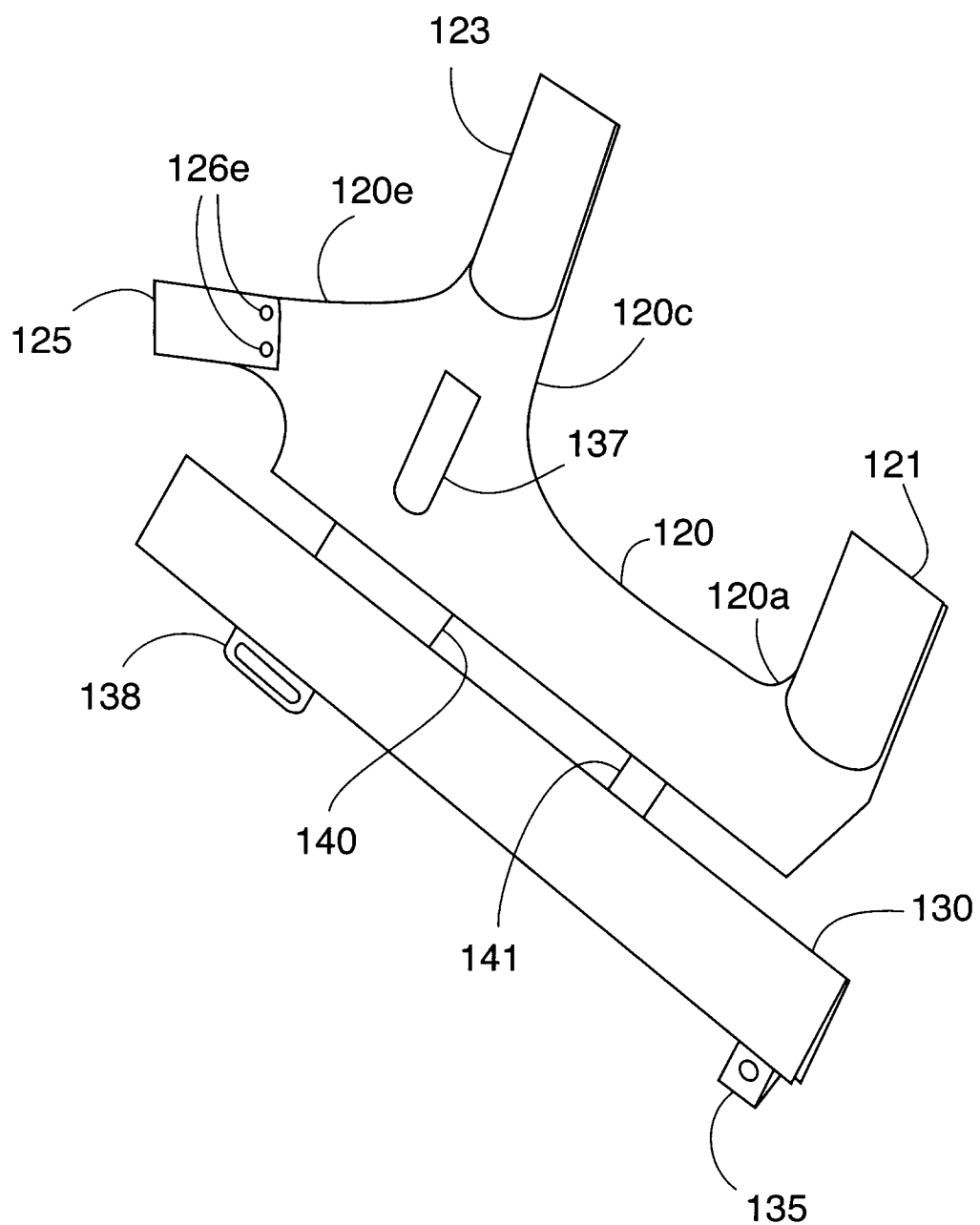
FIG. 9 is a front view of the embodiment from FIG. 9, showing the tubing harness unfastened and unfolded from the safety vest component.

As shown in FIGS. 3-6, the tubing safety vest 10 is installed about an infant's torso by placing the infant 60 onto the vest component 20. The first set of flaps 21a, 21b is secured around the infant's upper right thigh, the second set of flaps 22a, 22b is secured about the infant's upper chest, while the third set of flaps 23a, 23b is secured about the infant's right shoulder and arm pit. Those skilled in these arts will understand that if so desired, the first set of flaps 21a, 21b may be alternatively secured around the infant's upper left thigh, and the third set of flaps 23a, 23b about the infant's left shoulder and arm pit, and thus have the tubing harness positioned on the back of the subject. When the vest component 20 has been installed about the subject's torso, it is suitable for the tubing harness component 30 to be situated about and along the front-facing side of the subject as shown in FIGS. 4 and 6. The tubing harness 30 is opened by separating flaps 31a, 31b (FIG. 5) and as shown in these illustrations, an IV tubing 55 and a ventilator tubing 51 are positioned within the tubing harness 30 after which, the flaps 31a, 31b are folded together and releasably secured with fastening devices provided therefore. It is suitable for the IV tubing 55 extending from the top of the tubing harness 30 about the subject's shoulder to extend to the IV insertion site on the subject's right arm, and for the respirator tubing 51 extending from the top of the tubing harness 30 about the subject's shoulder to extend to the respirator mask 50 releasably attached to the subject's face. Thus, the IV tubing 55 and respirator tubing 51 extending from the bottom of the tubing harness 30 are routed to the IV pouch (not shown) and ventilation apparatus (not shown).

When installed on an infant or juvenile subject, the tubing harness is configured to contain and retain therein the medical treatment delivery tubing and/or cabling close to the subject's torso while enabling extension of the tubing and cabling from the upper end of the tubing harness 30 to selected IV and/or respirator installation sites on the subject's body. Since the opposite ends of the medical treatment delivery tubing exit the bottom end of the tubing harness 30 about the subject's upper thigh area and then extend to the treatment supply components (not shown), entanglement of the tubing about the subject's head, neck and throat areas is prevented, even during the subject's moving about on horizontal surfaces exemplified by cribs, beds and the like. It is within the scope of the present invention to optionally provide reel-like or alternatively spring-like devices configured to feed-out and retract medical delivery tubing from the treatment supply components to enable the subject to comfortably move about in various supine positions with medical treatment tubings attached to their bodies while sleeping, resting or playing. Furthermore, those skilled in these arts will understand that the tubing safety vests of the present invention enable adults to safely and comfortably pick up and handle juvenile subjects having medical treatment tubings attached to their bodies, without stressing and disrupting the tubing attachment points to the subject's body.

Another exemplary embodiment of the present invention is shown in FIGS. 7-13. The medical tubing safety vest 100 generally comprises a vest component 120 provided with a first flap 120a positioned about the lower end of the vest component, a pair of flaps 120b, 120c positioned about the upper end of the vest component, and a pair of flaps 120d, 120e extending upward from about the upper end of the vest component 120. The vest component 120 may comprise a washable fabric-type material or alternatively, may comprise a disposable fabric-like material. The lower flap 120a and one of each pair of the upper flaps, for example flaps 120c, 120e, are provided with stretchable resilient extensions 121, 123, 125 respectively, securely mounted at their proximal ends to the distal ends of the flaps. For illustration purposes, the distal ends of the resilient extensions in this example are provided with demountable attachment devices exemplified by Velcro® strips 122, 124 on extensions 121, 123 respectively, and by male and female snaps 126a, 126b on extension 125. The lower flap 120a and its stretchable extension 121 are configured to encircle and securely encase the upper thigh area of one of the wearer's legs. The upper set of flaps 120a, 120b and stretchable extension 123 are configured to encircle and securely encase the wearer's upper chest area. The upwardly extending set of flaps 120d, 120e and stretchable extension 125 are configured to encircle and securely encase one of the wearer's upper shoulder—armpit areas. Although Velcro® strips and snaps are shown in the accompanying drawings, other suitable releaseably cooperating fastening devices such as exemplified by: (a) buttons and buttonholes, (b) hook and eye clasps, (e) adhesive strips, and the like, may be used to securely but releasably encircle and encase a subject's torso. It is also suitable to provide a plurality of cooperating devices on each of the extension 121, 123, 125 thereby providing a plurality of fastening options to adjustably accommodate anatomical variations amongst subjects, and also, making it possible to tighten or loosen the vest component about the subject for safety and/or comfort.

Figure 10:
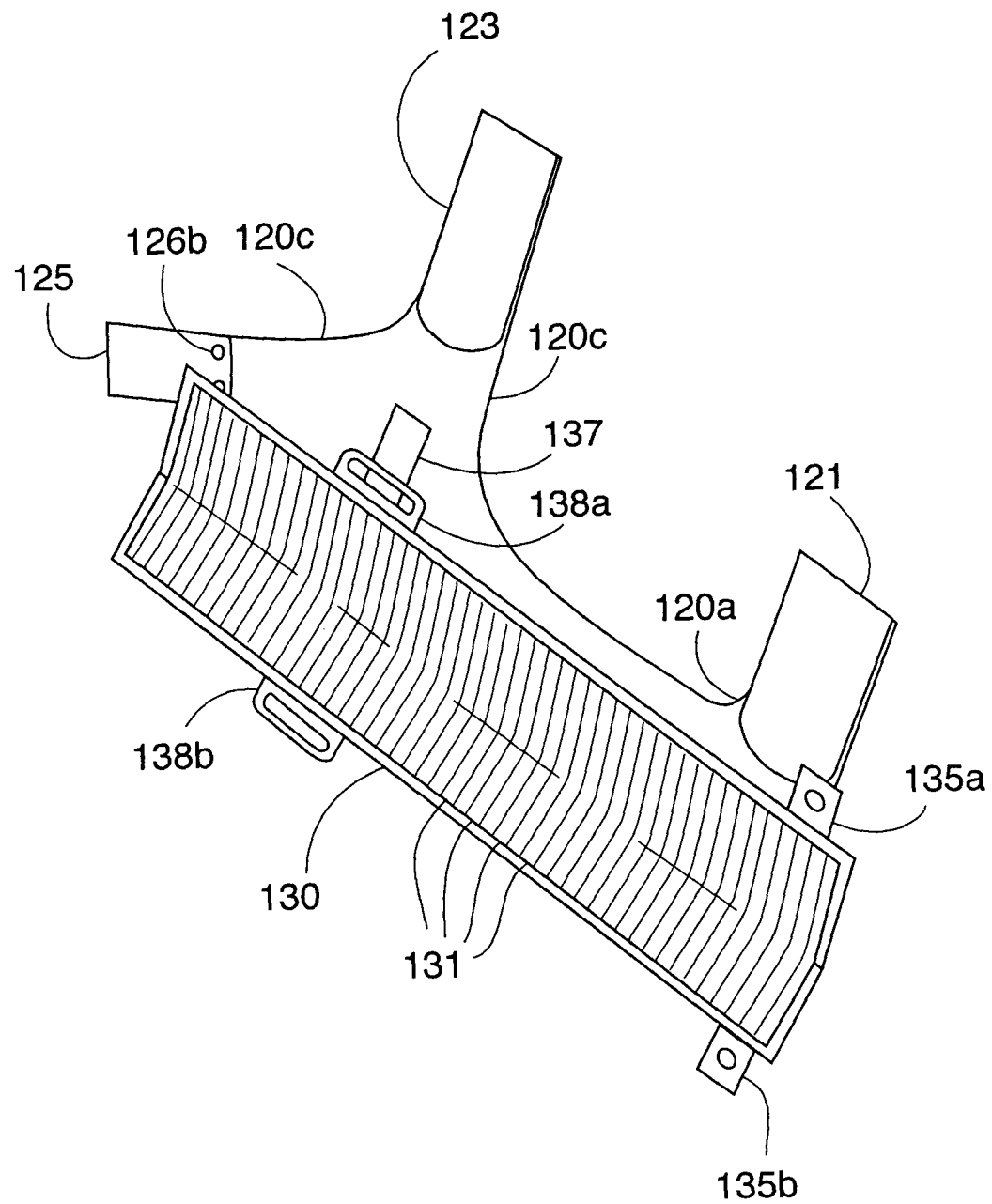
FIG. 10 is a front view of the embodiment from FIG. 10 showing the tubing harness opened for receiving and/or removing therefrom medical treatment delivery tubing and/or medical monitoring cables.
Figure 11:
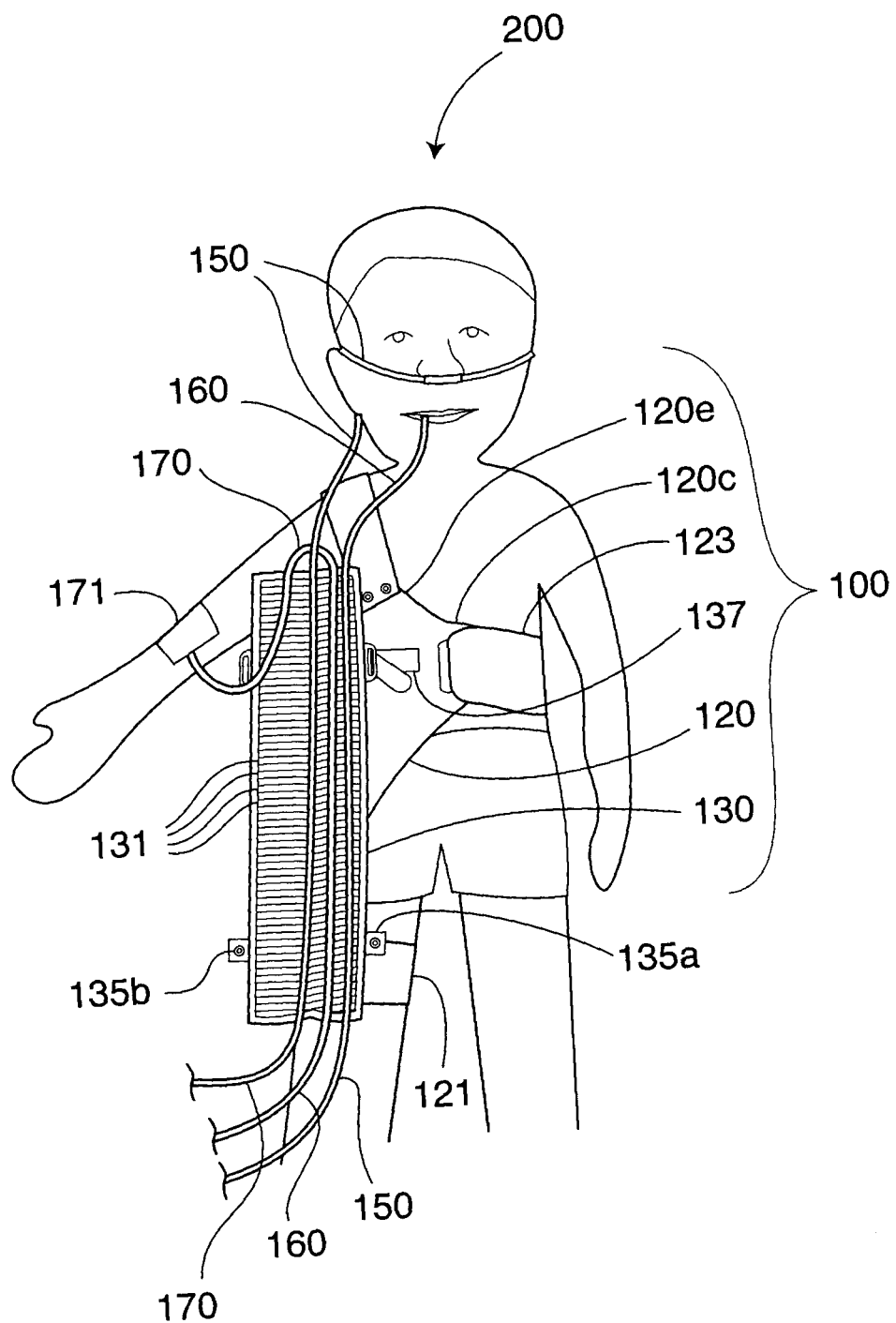
FIG. 11 is a front view of an another exemplary embodiment of a medical treatment delivery tubing safety vest of the present invention, with the vest component securely fastened about a juvenile child and the tubing harness opened for receiving medical tubing and cabling.
Figure 12:
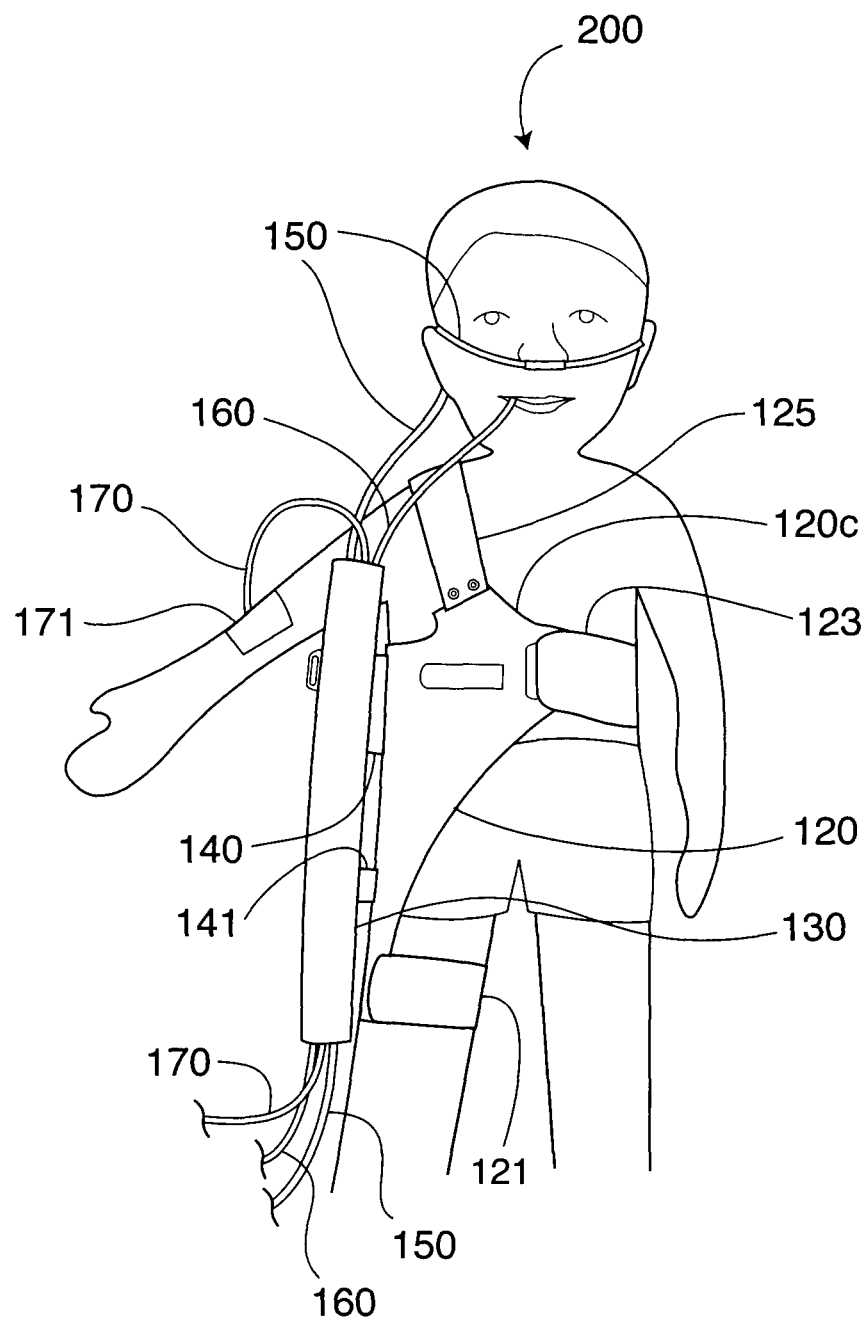
FIG. 12 is a front view of the tubing safety vest from FIG. 11, shown with the tubing harness secured about the medical tubing.
Figure 13:
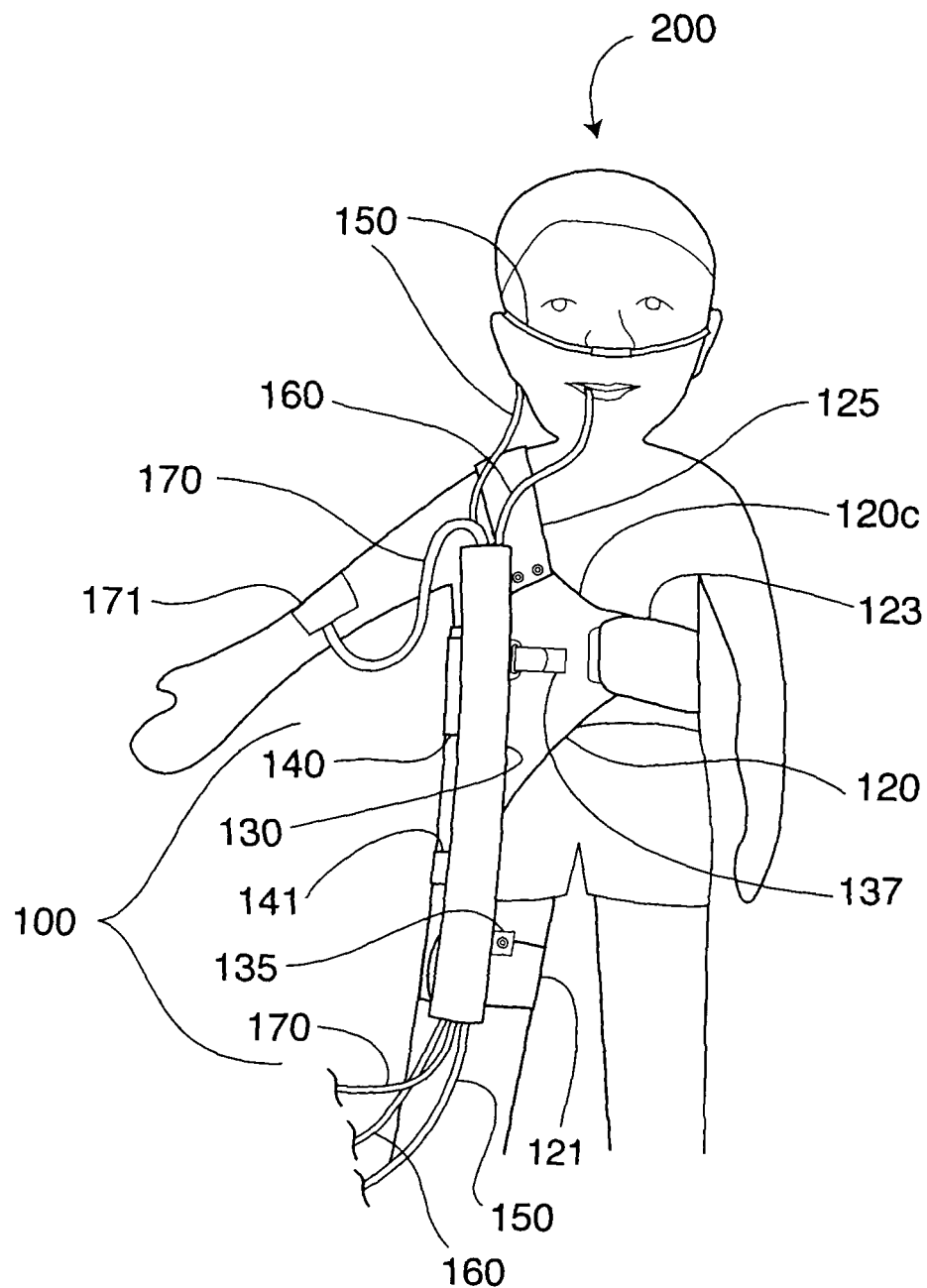
FIG. 13 is a front view of the tubing safety vest from FIG. 11, shown with the tubing harness secured to the vest component.

The tubing harness 130 is attached to the vest component 120 by at least one strip 140 of flexible material, and optionally a second strip 141. The two strips 140, 141 comprise a material exemplified by fabrics comprising plastic-coated fibres, are each securely engaged at one end to the vest component 120 and at the other end to the tubing harness 130. The two strips 140, 141 serve as hinges for moving the closed tubing harness 130 away from, and from the front to the back of the vest component 120, and are referred to hereinafter as hinges 140, 141. The tubing harness is disengagibly securable to the front or the back of the vest component 120 by a suitable fastening device as exemplified in FIGS. 8-9, wherein one end of a Velcro® strip 137, with its other end secured to the vest component, is passed through a rectangular ring 138 provided on the tubing harness 130, and then is engaged with its secured end. As shown in FIG. 10, the rectangular ring 138 may comprise two halves 138a, 138b that snap together to secure the edges of the tubing harness 130 together. The edges of the tubing harness 130 are provided with at least one more fastening device 135 exemplified by two-piece snaps 135a, 135b and 136a, 136b. It is to be noted that in this exemplary embodiment, the two-piece snap 136a, 136b is positioned such that the tubing harness is securely attached to the vest component 120 about the lower flap 120a and its stretchable extension 121 approximate the upper thigh area of the wearer's legs. In this exemplary embodiment, at least some of the inner surface of the tubing harness 130 is provided with strips of "sticky" materials 131 exemplified by silicone strips, double-sided adhesive strips and the like, for the purpose of engaging and retaining thereagainst tubing and/or cabling placed therein. Alternatively, the inner surface of the tubing harness may be provided with an elongate overlay extending along the length of the tubing harness (not shown) wherein the elongate overlay is configured with at least one channel extending therealong. The channel is configured to receive and releasingly engage therein at least one of a medical tubing or cabling. The elongate overlay may optionally configured with a plurality of channels extending therealong, wherein each channel is configured to receive and releasingly engage therein at least one of a medical tubing or cabling.

It is to be noted that the configuration of the vest component enables its installation about a subject by placing the vest on to a subject so that the flaps encircle one of the subject's thighs, the corresponding shoulder—armpit area, and their upper chest. For convenience of the caregivers and depending on the medical need, the vest may be positioned on the subject in such a way that the upper and lower flaps encircle their thigh and shoulder on their right side, or alternatively, such that that the upper and lower flaps encircle their thigh and shoulder on their left side. It is also suitable for a subject to be placed stomach down onto the vest component so that the flaps encircle one of the subject's thighs, their corresponding shoulder—armpit area, and their upper back. Regardless of the way that the tubing safety vest is installed about a subject, the tubing safety vest will not slip or slide around the subject as they may move about, nor will it tortionally twist about the subject's body.

While this invention has been described with respect to the exemplary embodiments, it is to be understood that various alterations and modifications can be made to components and the applications of the tubing safety vest within the scope of this invention, which are limited only by the scope of the appended claims.

The invention claimed is:

1. A safety vest for securing medical tubing and cables relative to a subject, the safety vest comprising:
   a vest component comprising a body-encompassing component cooperable with a plurality of releasably securable flaps, the vest component being configured for demountable installation about a torso of the subject;

an elongate tubing harness operable from an open position to a closed position in which the tubing harness is configured to releasably receive and retain therethrough at least one of said medical tubing and cables;

at least one hinge component coupling the tubing harness to the vest component such that the tubing harness is movable relative to the vest component in the closed position of the tubing harness between two opposing sides of the vest component; and at least one fastening device arranged to disengagibly secure the tubing harness to the vest component with said at least one of said medical tubing and cables releasably received and retained therein in the closed position of the tubing harness in either one of the two opposing sides of the vest component.

2. A safety vest according to claim 1, wherein the vest component is configured to encompass one of a human infant torso, a human juvenile torso, and a human adult torso.

3. A safety vest according to claim 1, wherein the vest component is configured to encompass an animal torso.

4. A safety vest according to claim 3, wherein the animal torso is selected from the group consisting of canines, felines, equines, livestock, and exotic wildlife.

5. A safety vest according to claim 1, wherein at least a portion of said flaps comprises an expandable-retractable resilient material.

6. A safety vest according to claim 1, wherein said flaps further include at least one releasable cooperating devices selected from the group comprising, buttons, hooks and eyes, clasps, snaps, adhesive strips, and fabric hook-and-loop fasteners.

7. A safety vest according to claim 1, wherein the tubing harness comprises an elongate foldable fabric material, wherein the opposing elongate edges are provided with releasable cooperating devices selected from the group comprising, buttons, hooks and eyes, clasps, snaps, adhesive strips, and fabric hook-and-loop fasteners.

8. A safety vest according to claim 1, wherein the tubing harness component comprises a pliant material selected from the group comprising washable natural textiles, synthetic textiles, disposable sheet goods and combinations thereof.

9. A safety vest according to claim 1, wherein the inner surface of the tubing harness component is provided with a slip-resistant component.

10. A safety vest according to claim 9, wherein the slip-resistant component consists of at least one of an impregnated slip-resistant material, a plurality of inter-woven fibres each coated with a slip-resistant coating, a sheet of slip-resistant material engaged with the inner surface of the tubing harness component, and a plurality of strips each comprising a slip-resistant material, said plurality of strips engaged with the inner surface of the tubing harness component.

11. A safety vest according to claim 1, wherein the inner surface of the tubing harness component is selectively engaged with an elongate overlay having a length, said elongate overlay further comprising at least one channel extending along said length, said channel being arranged for receiving at least one of said medical tubing and cables.

12. A safety vest according to claim 11, wherein the elongate overlay is configured with a plurality of channels extending along said length.

13. A safety vest according to claim 1, wherein said elongate tubing harness encircles said at least one of said medical tubing and cables along said length of said vest component.

14. A safety vest according to claim 1 wherein the two opposing sides of the vest component correspond to front and back sides of said torso respectively.

* * * * *